(12) United States Patent
Brueckner et al.

(10) Patent No.: US 9,573,131 B2
(45) Date of Patent: Feb. 21, 2017

(54) CARTRIDGE FOR DISPENSING A FLUID COMPRISING A REAGENT

(71) Applicant: Roche Diagnostics Operations, Inc., Indianapolis, IN (US)

(72) Inventors: Thorsten Brueckner, Schriesheim (DE); Peter Koltay, Freiburg (DE); Norbert Oranth, Voerstetten (DE); Juergen Spinke, Lorsch (DE); Laurent Tanguy, Freiburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/530,857

(22) Filed: Nov. 3, 2014

(65) Prior Publication Data

US 2015/0224500 A1    Aug. 13, 2015

Related U.S. Application Data

(63) Continuation of application No. PCT/EP2013/059461, filed on May 7, 2013.

(30) Foreign Application Priority Data

May 8, 2012  (EP) .................................... 12167111

(51) Int. Cl.
*A61J 1/06* (2006.01)
*B01L 3/00* (2006.01)
(Continued)

(52) U.S. Cl.
CPC .. *B01L 3/52* (2013.01); *B01L 1/00* (2013.01); *B01L 3/523* (2013.01); *B01L 5/00* (2013.01);
(Continued)

(58) Field of Classification Search
CPC ................. A61J 1/06; B01L 3/00; G01N 1/10
USPC ......... 422/554, 521, 68.1, 502, 503; 436/43, 436/180
See application file for complete search history.

(56) References Cited

U.S. PATENT DOCUMENTS

| 4,748,522 A | 5/1988 | Takahashi et al. |
| 5,078,970 A | 1/1992 | Teodorescu et al. |

(Continued)

FOREIGN PATENT DOCUMENTS

| EP | 1959257 A2 | 8/2008 |
| JP | 57-011756 A | 6/1982 |

(Continued)

OTHER PUBLICATIONS

International Search Report issued Aug. 16, 2013 in Application No. PCT/EP2013/059461, 4 pages.

*Primary Examiner* — Brian J Sines
(74) *Attorney, Agent, or Firm* — Roche Diagnostics Operations, Inc.

(57) ABSTRACT

A cartridge for dispensing a fluid is presented. The cartridge comprises a reservoir chamber for receiving the fluid and for receiving a ventilation gas. The reservoir chamber comprises an inlet for receiving the ventilation gas and an outlet for dispensing the fluid. At least a portion of the reservoir chamber is filled with the ventilation gas when in an operating position. The inlet is located in the portion being filled with the ventilation gas. The fluid comprises a reagent. The cartridge further comprises a baffle for restricting gas diffusion through the inlet. The reservoir chamber receives the ventilation gas via the baffle. The inlet is maintains a constant gas pressure within the portion of the reservoir chamber that is being filled with the ventilation gas.

25 Claims, 8 Drawing Sheets

(51) Int. Cl.
 G01N 1/10 (2006.01)
 G01N 35/10 (2006.01)
 B01L 1/00 (2006.01)
 B01L 5/00 (2006.01)

(52) U.S. Cl.
 CPC ... *G01N 35/1002* (2013.01); *B01L 2200/0684* (2013.01); *B01L 2200/141* (2013.01); *B01L 2300/048* (2013.01); *B01L 2300/0681* (2013.01); *B01L 2400/086* (2013.01); *Y10T 436/11* (2015.01)

(56) References Cited

U.S. PATENT DOCUMENTS

| | | | |
|---|---|---|---|
| 5,660,796 A | | 8/1997 | Sheehy |
| 6,242,266 B1 * | | 6/2001 | Schleifer et al. ............ 436/518 |
| 8,206,648 B2 | | 6/2012 | Sattler |
| 8,486,346 B2 | | 7/2013 | Blackwell et al. |
| 9,068,566 B2 * | | 6/2015 | Ivri |
| 2010/0015009 A1 | | 1/2010 | Wallace et al. |
| 2011/0303760 A1 | | 12/2011 | Joshi et al. |

FOREIGN PATENT DOCUMENTS

| | | |
|---|---|---|
| JP | S62-199675 U | 2/1986 |
| JP | S63-082959 A | 4/1988 |
| JP | 04-034660 U | 5/1990 |
| JP | 3007633 U | 11/1994 |
| JP | H09-043251 A | 8/1995 |
| JP | 2000-009734 A | 1/2000 |
| JP | 2000-137036 A | 5/2000 |
| JP | 3141762 U | 5/2008 |
| WO | 2006/005923 A1 | 1/2006 |
| WO | 2007/122387 A3 | 11/2007 |

* cited by examiner

US 9,573,131 B2

CARTRIDGE FOR DISPENSING A FLUID COMPRISING A REAGENT

CROSS-REFERENCE TO RELATED APPLICATIONS

This application is a continuation of PCT/EP2013/059461, filed May 7, 2013, which is based on and claims priority to EP 12167111.9, filed May 8, 2012, which is hereby incorporated by reference.

BACKGROUND

The present disclosure generally relates to the dispensing of fluids comprising a reagent and, in particular, to cartridges for dispensing fluids.

In medical laboratories, in vitro diagnostics are commonly performed on biological samples. Such tests may be performed manually using pipettes or maybe performed using an automatic analyzer. Automatic analyzers may automatically add reagents to the biological sample and may measure one or more physical properties of the biological sample during analysis.

SUMMARY

According to the present disclosure, a cartridge for dispensing a fluid is presented. The cartridge comprises a reservoir chamber for receiving the fluid and for receiving a ventilation gas. The reservoir chamber comprises an inlet for receiving the ventilation gas and an outlet for dispensing the fluid. At least a portion of the reservoir chamber is filled with the ventilation gas when in an operating position. The inlet is located in the portion filled with the ventilation gas. The fluid comprises a reagent. The cartridge further comprises a baffle for restricting gas diffusion through the inlet. The reservoir chamber receives the ventilation gas via the baffle. The inlet maintains a constant gas pressure within the portion of the reservoir chamber that is filled with the ventilation gas.

In accordance with one embodiment of the present disclosure, the cartridge further comprises a cap for sealing the inlet.

In accordance with another embodiment of the present disclosure, the cartridge further comprises a dispenser for dispensing the fluid. The dispenser receives the fluid from the outlet.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
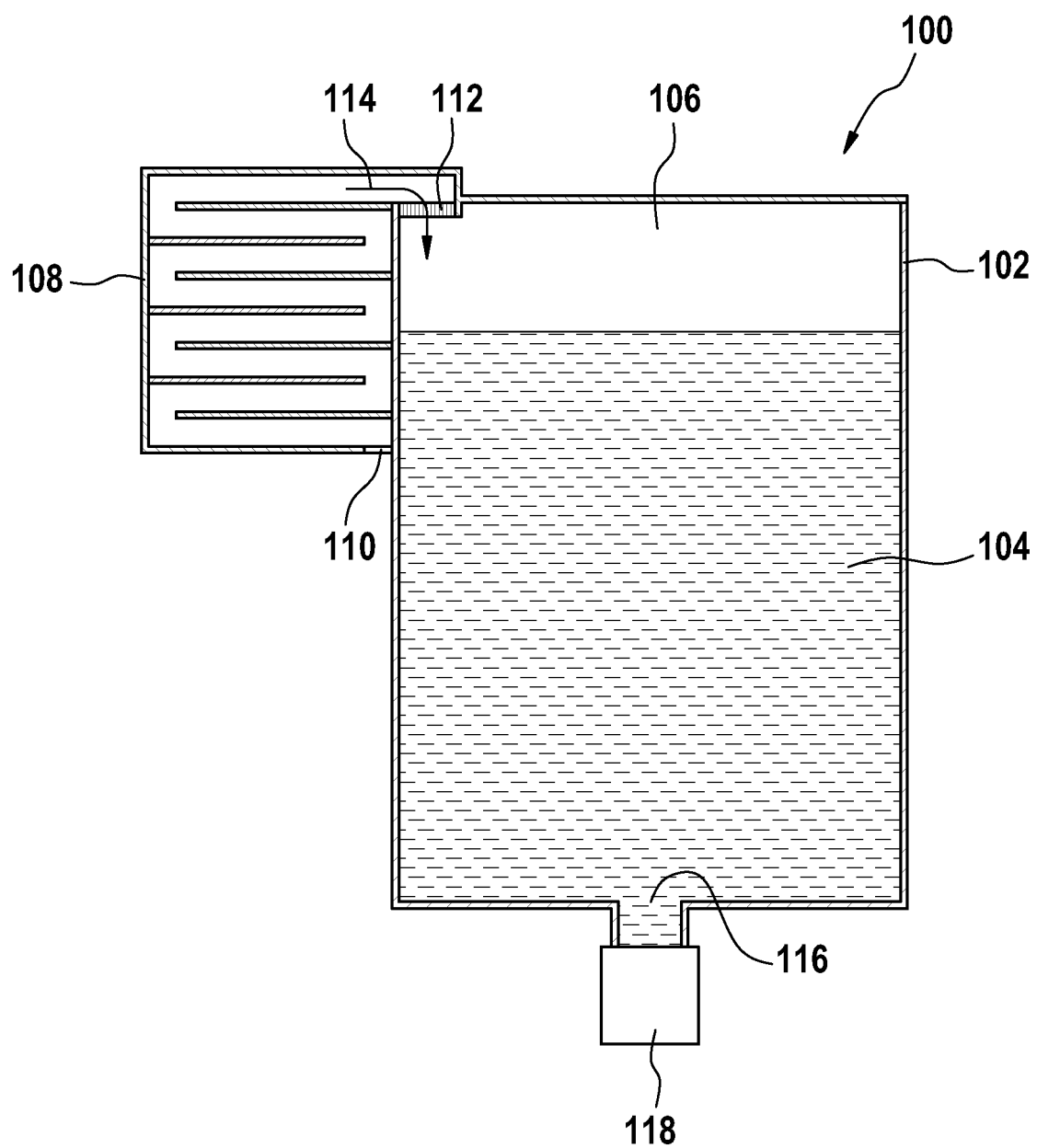
FIG. 1 illustrates a cartridge according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A cartridge for dispensing a fluid is presented. The cartridge can comprise a reservoir chamber for receiving the fluid. The reservoir chamber can also receive a ventilation gas. The reservoir chamber can comprise an inlet for receiving the ventilation gas. There can also be an outlet for dispensing a fluid from the reservoir. At least a portion of the reservoir chamber can be filled with the ventilation gas when the cartridge is placed in an operating position. The inlet can be located in the portion being filled with the ventilation gas. The fluid can comprise a reagent. The cartridge can further comprise a baffle for restricting gas diffusion through the inlet. The reservoir chamber can receive the ventilation gas via the baffle. Since the ventilation gas is provided directly to the gas within the reservoir, there can be no bubble formation to cause variations of the pressure within the reservoir chamber. In this embodiment, the baffle can provide the ventilation gas directly to the portion of the reservoir chamber being filled with the ventilation gas. Embodiments of the invention may therefore have the advantage that there can always be equilibrium in pressure between the outside of the cartridge and the gas within the reservoir chamber. Embodiments of the invention may also have the advantage that the baffle can reduce the diffusion of gases into the reservoir chamber which may damage or degrade the fluid. The baffle may also reduce evaporation of the fluid within the reservoir chamber because the diffusion of gas out of the reservoir chamber can also be reduced.

A controller as used herein can encompass a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein can encompass any device comprising a processor. A 'processor' as used herein can encompass an electronic component which can be able to execute a program or machine executable instruction.

A 'computer-readable storage medium' as used herein can encompass any tangible storage medium which may store instructions which can be executable by a processor of a computing device. The computer-readable storage medium may be referred to as a computer-readable non-transitory storage medium.

'Computer memory' or 'memory' can be an example of a computer-readable storage medium. Computer memory can be any memory which can be directly accessible to a processor or other controller. 'Computer storage' or 'storage' is an example of a computer-readable storage medium. Computer storage can be any non-volatile computer-readable storage medium.

A 'user interface' as used herein can be an interface which can allow a user or operator to interact with a computer or computer system.

A 'hardware interface' as used herein can encompass an interface which can enable a processor or other controller to interact with and/or control an external computing device and/or apparatus. A hardware interface may allow a processor to send control signals or instructions to an external computing device and/or apparatus.

The cartridge can comprise a reservoir chamber for receiving a fluid and for receiving a ventilation gas. A ventilation gas as used herein can encompass a gas which can be used to equalize the pressure outside of the reservoir chamber and inside the reservoir chamber when fluid is removed from the reservoir chamber. The reservoir chamber can comprise an inlet for receiving the ventilation gas and an outlet for dispensing the fluid. At least a portion of the reservoir chamber can be filled with the ventilation gas when in an operating position. The inlet can be located in the portion being filled with the ventilation gas. In other words, when the cartridge is in an operating position, ventilation gas can be added to the reservoir chamber at a location where there may be ventilation gas already or which may be immediately filled with the ventilation gas. The fluid can comprise a reagent. A reagent as used herein can be a substance or compound that can be added to a chemical system in order to bring about a chemical or biochemical reaction or added to see if a reaction occurs.

The cartridge can further comprise a baffle for restricting gas diffusion through the inlet. The reservoir chamber can receive the ventilation gas via the baffle. A baffle as used herein can encompass a structure which can cause gas to follow a particular path in order to reach the inlet. The baffle can restrict the diffusion of gas in and/or out of the inlet. As such the gas diffusion as used herein may refer to the diffusion of ventilation gas into the cartridge and/or gas already present in the reservoir chamber from diffusing out. This embodiment may be advantageous because it may preserve the lifetime of the reagent within the cartridge. For instance, depending upon the reagent constituents of the ventilation gas may cause the reagent to lose effectiveness or to lose its chemical reactivity; also gas inside the reservoir chamber may contain vapors from the fluid. The baffle can restrict the diffusion of the fluid vapor out of the inlet also. This may help to prevent the concentration of a particular reagent from changing.

In another embodiment, the cartridge can comprise a cap for sealing the inlet. The cap may be moved into an open position for opening the inlet. In some embodiments, the cap may seal the inlet directly, that can be the sealing effect of the cap can be at the inlet. In other embodiments, the cap can seal the baffle or a portion of the baffle. This can indirectly seal the inlet.

A cap as used herein may in some embodiments be a mechanical part to open or close the inlet. Examples of caps may include, a removable piece of plastic, a piece of tape, and a mechanical part which can interlock with the cartridge such as a screw cap.

In another embodiment, the inlet can maintain a constant pressure within the portion of the reservoir chamber being filled with the ventilation gas. This embodiment may be beneficial because maintaining the pressure at a constant value can enable more accurate dispensing of the fluid. In some embodiments, the inlet can maintain a constant pressure within the portion of the reservoir chamber being filled with the ventilation gas when dispensing fluid.

For example, an inlet which is submerged within the fluid is known in the art. Gas enters into the cartridge reservoir by bubbling at the inlet. This bubbling causes small variations within the reservoir. This may lead to inconstancies of the amount of fluid dispensed, particularly if the amount of fluid is within a micro-fluidic range. Embodiments of the present disclosure may provide for more accurate dispensing of fluid.

In another embodiment, the inlet can maintain a constant pressure within the portion of the reservoir chamber being filled with the ventilation gas when the reservoir chamber is between about 10 and about 90 percent full with the fluid and in another embodiment, between about 20 and about 80 percent full with the fluid. This embodiment may be beneficial, because maintaining the pressure at a constant value can enable more accurate dispensing of the fluid.

In some embodiments, the cartridge may comprise a filling inlet for filling the fluid into the reservoir chamber.

In some embodiments, the ventilation gas may be normal atmospheric air. In some embodiments, the baffle can be open to the atmosphere.

In another embodiment, the cap can be moved to an open position to open the inlet. The cap may be removable or may be movable but fixed to the cartridge. In another embodiment, the cap can be moved to a closed position. This, for instance, may be useful for re-sealing the inlet. In another embodiment, the cap can be moved from the open position to the closed position. In another embodiment, the cap can be moved from the closed position to the open position.

In another embodiment, the cartridge can comprise a cap for sealing the inlet. The cartridge can form at least a portion of the baffle when the cap is open. This embodiment may be beneficial because after removal of the cap, placing the cap into an operating position can form a portion of the baffle.

In another embodiment, the cartridge can comprise threads for attaching the cap. The baffle can comprise a diffusion path formed in the threads. For example, the diffusion path can be a tube molded into the threads or a channel cut or molded on a surface of the threads. This embodiment may be beneficial because it may provide a cost effective means of providing the baffle and integrating it into an existing structure.

In another embodiment, the diffusion path can be a channel in the threads. The cartridge can further comprise a cap restraint for limiting the opening of the cap a predetermined amount. For example, the cap and a portion of the cartridge may each have tabs or blocks on them. When the cap is open say a quarter or a half or three quarters turns, it may prevent the cap from turning any further. This embodiment may be beneficial because it may provide a means of opening the threads a predetermined amount so that the diffusion along the channel can be predictable and consistent between different cartridges.

In another embodiment, the baffle can be at least partially formed on an exterior surface of the cartridge. This embodiment may be beneficial because it may provide a contact means of integrating a baffle into a cartridge.

In another embodiment, the baffle can comprise a tube mounted on the exterior surface.

In another embodiment, the baffle can be at least partially formed within the reservoir chamber. This embodiment may be beneficial because the baffle may be added to an existing cartridge or a baffle may be tailored to a specific fluid. For instance, some fluids may need a baffle which can restrict diffusion greater than another one in order to preserve the reagent.

In another embodiment, the baffle can comprise a tube located at least partially within the reservoir chamber. This embodiment may be beneficial because the amount of tube within the reservoir chamber may be easily adjusted during manufacture of the cartridge.

In another embodiment, the tube can comprise an opening and the inlet. The opening may be directly open to the atmosphere or a gas supply. There may be a gas filter at the inlet.

The cap can, for example, be mounted with threads. When the cap is in a closed position, it can push against and seal the inlet. When the cap is unscrewed, it can move away from the inlet and open it.

In another embodiment, the tube can have a length-to-diameter ratio of at least 2. In another embodiment, the tube can have a length-to-diameter ratio of at least 100.

In another embodiment, at least part of the cartridge can be injected molded. The baffle can be formed at least partially by the part.

In another embodiment, the baffle can comprise a gas filter. The gas filter may be beneficial because in some embodiments it may help to further reduce diffusion through the inlet. In some embodiments, the gas filter may have micro-pores to only let gas through. In some embodiments, the filter may be hydrophobic. In other embodiments, the gas filter may be porous forms of polytetrafluoroethylene (PTFE), carbon fibers, carbon fibers coated with PTFE, polymer fibers, fluoropolymer fibers or combinations thereof. This embodiment may be beneficial also from the aspect that the gas filter may help to keep the fluid within the reservoir chamber.

In another embodiment, the cartridge further can comprise the fluid. In another embodiment, the fluid can comprise a blood grouping reagent, a diluent, a solvent, a catalyst, an antibody, an enzyme, a recombinant protein, a virus isolate, a virus, a biological reagent, a protein, a salt, a detergent, a nucleic acid, an acid or a base.

In another embodiment, the fluid can comprise a dispersion. A dispersion as used herein can encompass particles or particulates suspended within the fluid.

In another embodiment, the fluid may comprise latex particles, nanoparticles or magnetic particles.

In another embodiment, the cartridge can further comprise a dispenser for dispensing the fluid. The dispenser can receive the fluid from the outlet. In some embodiments, the dispenser may be a microfluidic dispenser. In other embodiments, the dispenser may be or comprise a nozzle. For instance, the dispenser may be or comprise a straight tube or it may be or comprise a nozzle with one or more valves contained within it.

In another embodiment, the dispenser can dispense fluid at a rate independent of the baffle. In other words, the dispensing of the fluid may not be regulated or controlled by the baffle. For example, an apparatus for controllably releasing a substance is known. A regulator element restricts the flow of gas into the apparatus and effectively controls the release rate of a fluid. In contrast, embodiments of the present disclosure may dispense fluid at a rate that is effectively independent of the baffle. The baffle may have such a small effect on the rate of dispensing that the effect can be much smaller than the actual volume dispensed. This may enable more accurate dispensing of the fluid.

In another embodiment, the dispenser can be a microfluidic dispensing assembly.

In another embodiment, the dispenser can dispense any one of the following: volumes less than 10 µL, less than 500 nL, less than 200 nL, less than 100 nL, and less than 20 nL.

In another embodiment, the cap can be attached to cartridge. In another embodiment, the cap can be removed from the cartridge. In another embodiment, the cap can be movable between an open position and a closed position, wherein when in the open position the cap can open the baffle.

An automatic analyzer for holding or receiving a cartridge is presented. The automatic analyzer can comprise an actuator assembly for actuating the dispenser. The automatic analyzer can further comprise a controller for controlling the operation of the actuator assembly. The dispenser can be mechanically, pneumatically, magnetically, and/or electrically actuated. This can be dependent upon the implementation and how the dispenser is constructed. In an embodiment, the cartridge can be in an operating position when installed into the automatic analyzer.

A method of dispensing fluid with the automatic analyzer is presented. The method can comprise providing a cartridge. The cartridge can comprise a reservoir chamber. The reservoir chamber can be filled with the fluid. The fluid can comprise a reagent. The reservoir chamber can comprise an inlet for receiving a ventilation gas and an outlet for dispensing the fluid. The cartridge can further comprise a baffle for restricting gas diffusion through the inlet. The cartridge can further comprise a dispenser for dispensing the fluid. The method can further comprise installing the cartridge into an automatic analyzer in an operating position. The automatic analyzer can comprise an actuator assembly for actuating the dispenser. The method can further comprise receiving the fluid from the outlet using the dispenser. The method can further comprise operating the actuator assembly to dispense the fluid. The method can further comprise receiving the ventilation gas via the baffle at the inlet. The method can further comprise filling at least a portion of the reservoir chamber with the ventilation gas. The inlet can be located in the portion being filled with the ventilation gas. In another embodiment, the method can further comprise removing a seal from the baffle to provide air as the ventilation gas.

Referring initially to FIG. 1, FIG. 1 illustrates a cartridge. The cartridge 100 can comprise a reservoir chamber 102 for holding a fluid 104. The reservoir chamber 102 can only be partially filled with the fluid 104. There can be a region filled with gas 106 at the top of the reservoir chamber 102. Adjacent to the reservoir chamber 102 can be a baffle 108. The baffle 108 in this example can have a vent-to-atmosphere 110. Traveling through the baffle, there can be an optional gas filter 112 which can cover an inlet 114 to the reservoir chamber 102. The inlet 114 can provide ventilation gas to the gas filled portion 106 of the reservoir chamber 102. The inlet 114 can be attached to the baffle 108. The fluid 104 can exit the reservoir chamber 102 via an outlet 116. In this example, there can be an optional dispenser 118. The dispenser, in this embodiment, may either be a mechanism for pumping the fluid or it may simply be a nozzle or tube for dispensing the fluid.

Figure 2:
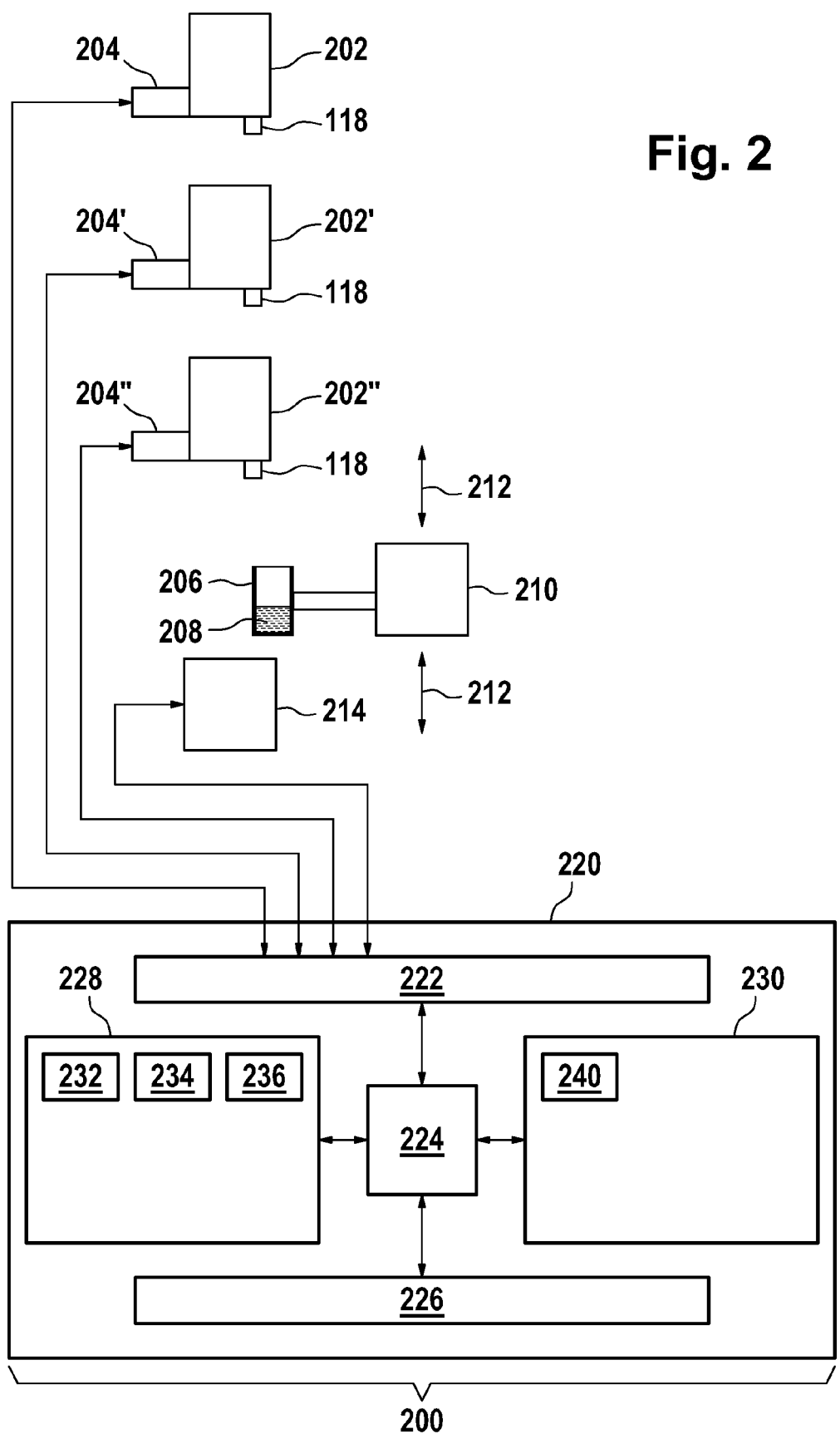
FIG. 2 illustrates an automatic analyzer according to an embodiment of the present disclosure.

FIG. 2 illustrates an automatic analyzer 200. This automatic analyzer is shown as having three cartridges 202, 202' and 202". There can be an actuator assembly 204 connected to cartridge 202. There can be an actuator assembly 204' attached to cartridge 202'. There can be an actuator assembly 204" attached to cartridge 202". The actuators 204, 204', 204" can be for actuating the dispenser 118 of the cartridges 202, 202', 202". The automatic analyzer 200 is shown as having a relative mover 210 which can provide relative movement 212 between a sample holder 206 and the cartridges 202, 202' and 202". The sample holder 206 is shown as containing a biological sample 208. The cartridges 202, 202', 202" may be used to add one or more fluids to the biological sample 208. The automatic analyzer 200 may optionally comprise a measurement system 214. The measurement system 214 may comprise one or more sensors for measuring a physical quantity or physical property of the biological sample 208. For example the measurement system 214 may comprise an NMR system, an optical transmission or reflectance measurement system, an electrochemical or optical sensor, a pH meter, a camera system or a chromatography system. The relative mover 210 can also move the sample holder 206 to the measurement system 214.

The arrangement of the cartridges 202, 202', 202" and the measurement system 214 is representative. The measurement system 214 may be alternatively also a part of the sample holder 206. In some embodiments, the sample holder 206 may remain in a fixed position and the cartridges 202, 202', 202" may move. The actuation systems 204, 204', 204" and the measurement system 214 are shown as being connected to a hardware interface 222 of a computer system 220. The computer system 220 can function as a controller for the automatic analyzer 200. The computer 220 is further shown as containing a processor 224 which can be able to control the operation and function of the automatic analyzer 200 using the hardware interface 222. The processor 224 is shown as further being connected to a user interface 226, computer storage 228 and computer memory 230. The computer storage 228 is shown as containing an analysis request 232. The analysis request 232 can contain a request to analyze the biological sample 208.

The computer storage 228 is shown as further containing sensor data 234 received from the measurement system 214. The computer storage 228 is shown as further containing an analysis result 236 which can be determined using the sensor data 234. The computer memory 230 can contain a control module 240. The control module 240 can contain computer executable code which can enable the processor 224 to control the operation and function of the automatic analyzer 200. For instance, the control module 240 may use the analysis request 232 to generate commands to generate and send to the actuation systems 204, 204', 204", the measurement system 214 and the relative movement system 210. The control module 240 may also generate the analysis result 236 using the sensor data 234.

Figure 3:
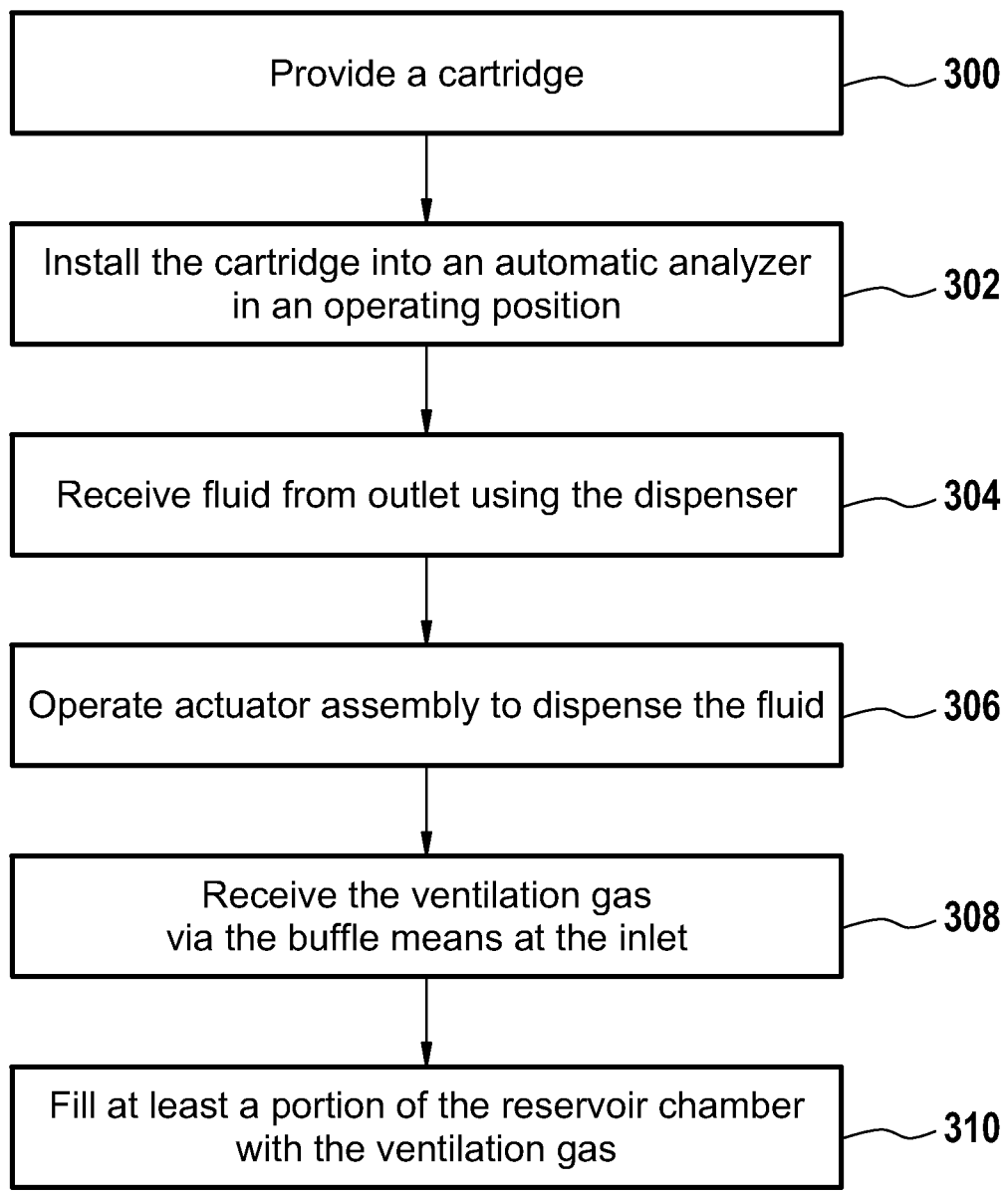
FIG. 3 illustrates a flow diagram which illustrates a method according to an embodiment of the present disclosure.

FIG. 3 shows a flow diagram which illustrates a method according to an embodiment of the invention. First in step 300, a cartridge can be provided. Next in step 302, the cartridge can be installed into an automatic analyzer and the cartridge can be in an operating position. Next in step 304, fluid can dispense, i.e. received, from the outlet using the dispenser. Next in step 306, the actuator center can dispense the fluid. Next in step 308, the ventilation gas can be received via the baffle at the inlet of the fluid reservoir. Finally in step 310, at least a portion of the reservoir chamber can be filled with the ventilation gas.

Figure 4:
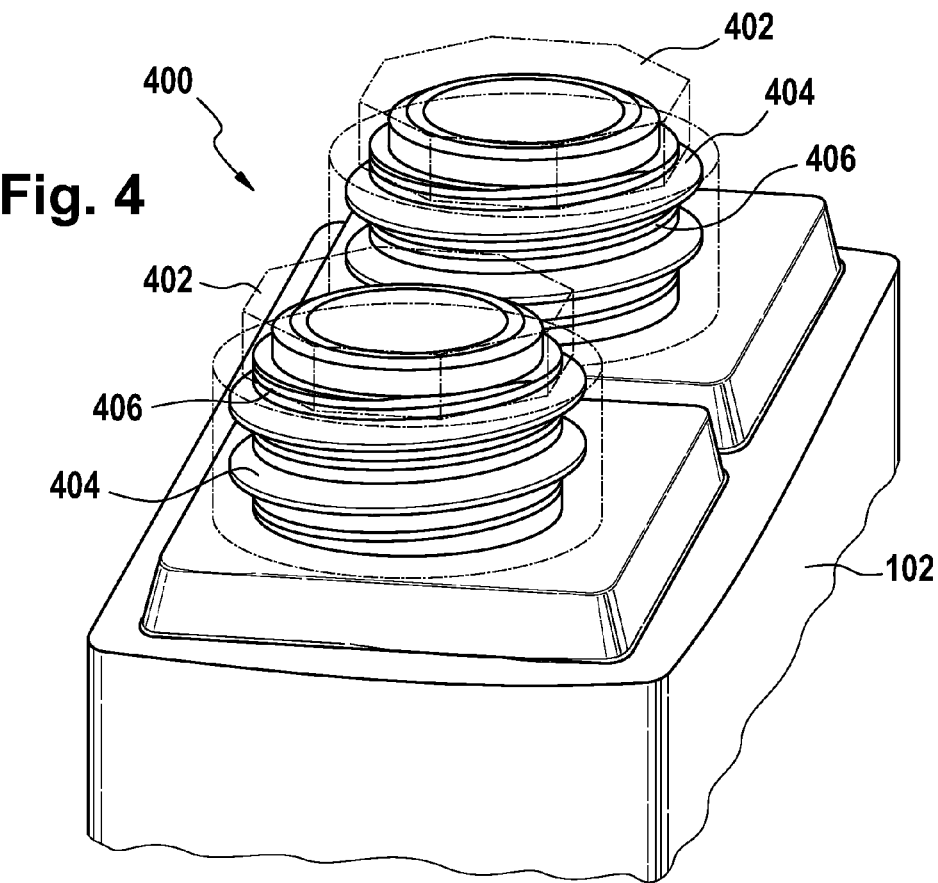
FIG. 4 illustrates a cartridge according to a further embodiment of the present disclosure.
Figure 5:
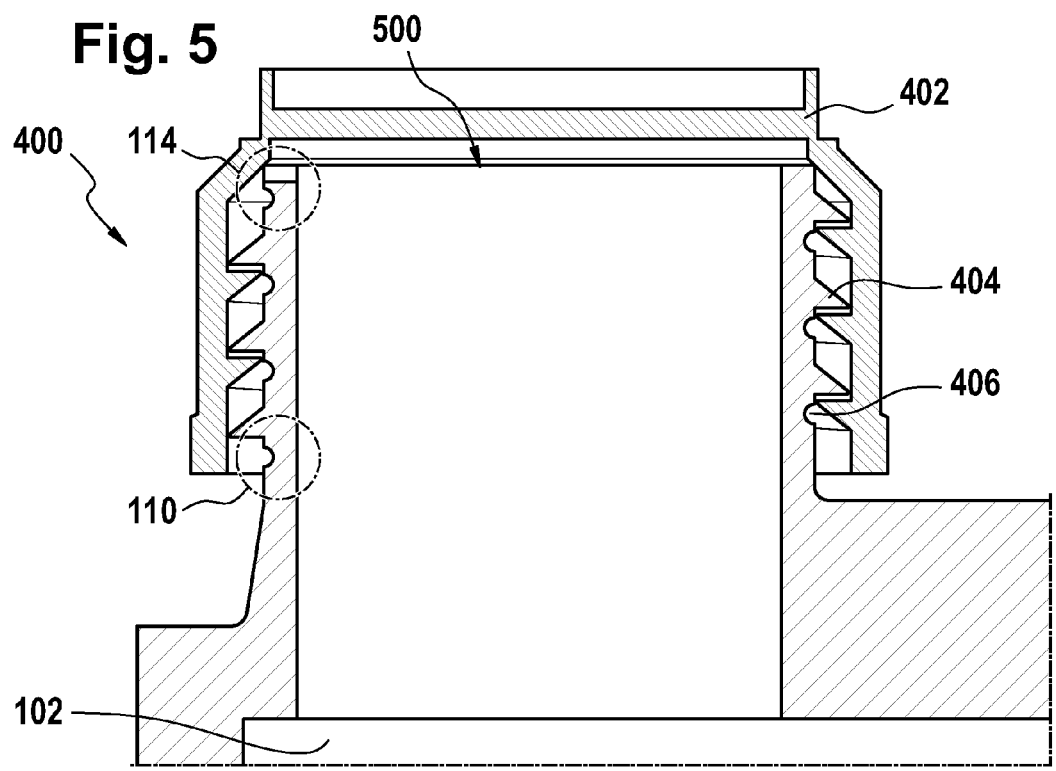
FIG. 5 further illustrates the cartridge shown in FIG. 4 according to an embodiment of the present disclosure.

FIGS. 4 and 5 show an alternative embodiment of a cartridge 400. In FIGS. 4 and 5 two cartridges can be integrated into a common housing. This cartridge 400 design can have a cap 402 that can be secured by threads 404. The reservoir chamber 102 can be sealed by the cap 402. There can be channels 406 cut or molded into the threads 404. When the cap 402 is open slightly, as is shown in FIG. 5, the channel 406 can form a vent-to-atmosphere 110. At the top of the threads 404, the gap between the cap 402 and the threads 404 can form the inlet 114. A gas filter may be stretched across the opening of the inlet 114 in some embodiments. The position is marked 500 in FIG. 5. When the cap 402 is closed, the reservoir chamber 102 can be sealed and the inlet 114 can be closed. When the cap 402 is opened, gas can diffuse into the channel 406. The amount the cap 402 is open may be controlled by placing a stop on the cap 402 and a corresponding stop on the reservoir chamber 102 to prevent the cap 402 from being opened too far.

Figure 6:
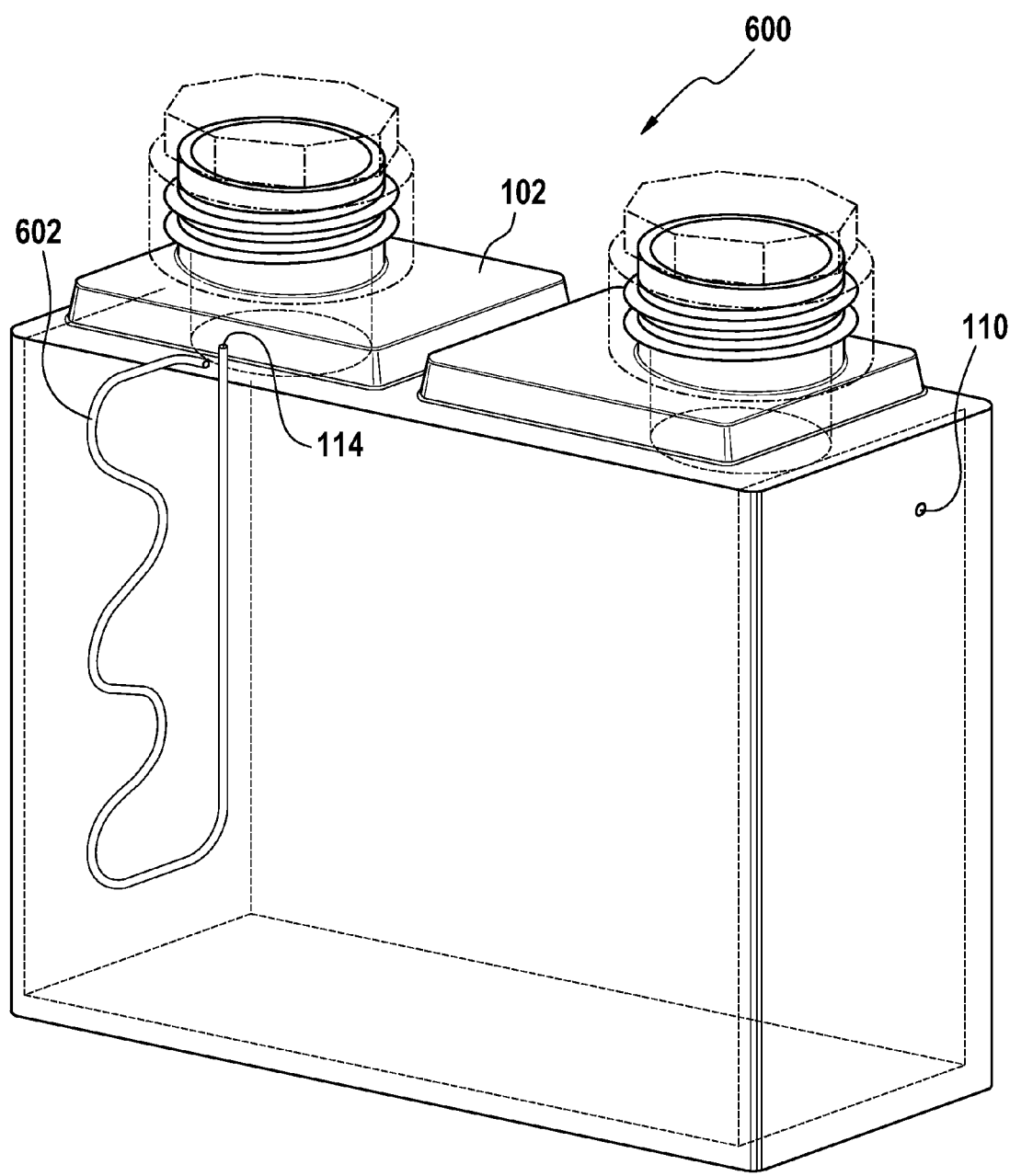
FIG. 6 illustrates a cartridge according to yet another embodiment of the present disclosure.
Figure 7:
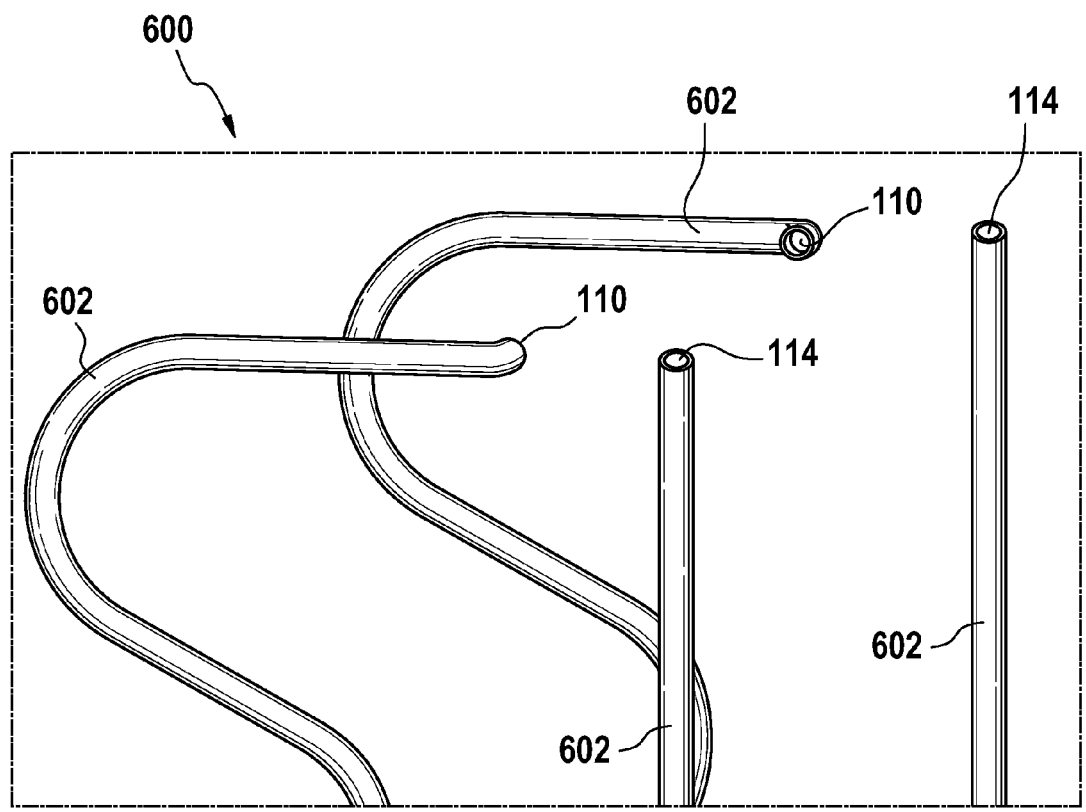
FIG. 7 illustrates the cartridge shown in FIG. 6 providing an view onto the exterior surface of the cartridge shown in FIG. 6 according to an embodiment of the present disclosure.

FIGS. 6 and 7 illustrate a cartridge 600 according to a further embodiment. In FIGS. 6 and 7, two cartridges can be integrated into a common housing. In the embodiments shown in FIGS. 6 and 7, a tube 602 that is either attached to the surface of the reservoir chamber 102 or is molded or partially molded into the reservoir chamber 102 can be used. The tubes 602 can have a vent-to-atmosphere 110 and follow a winding path on the outside of the cartridge 600. The tubes 602 can then be connected to the inlet 114 of the reservoir chamber 102.

Figure 8:
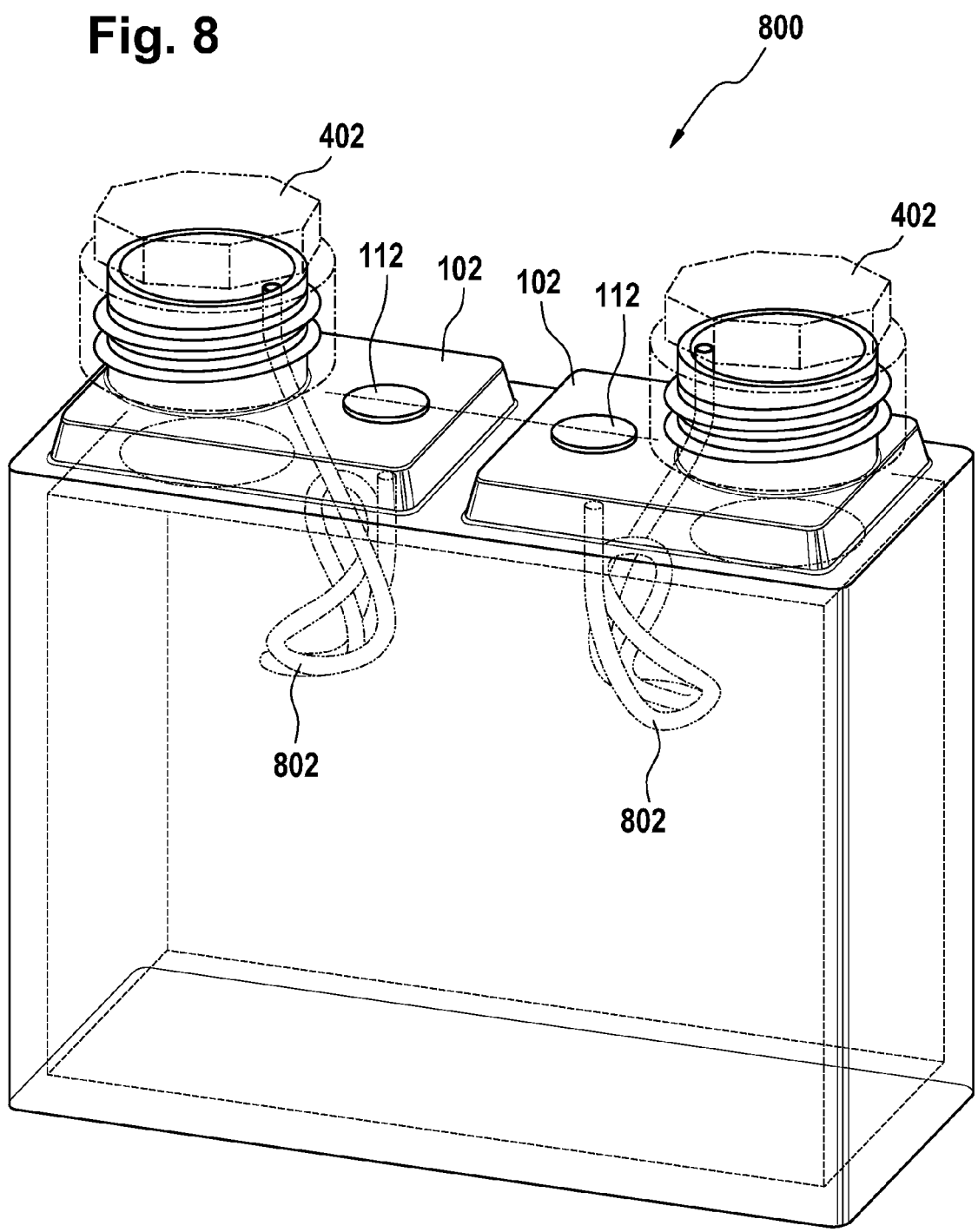
FIG. 8 illustrates a cartridge according to still another embodiment of the present disclosure.
Figure 9:
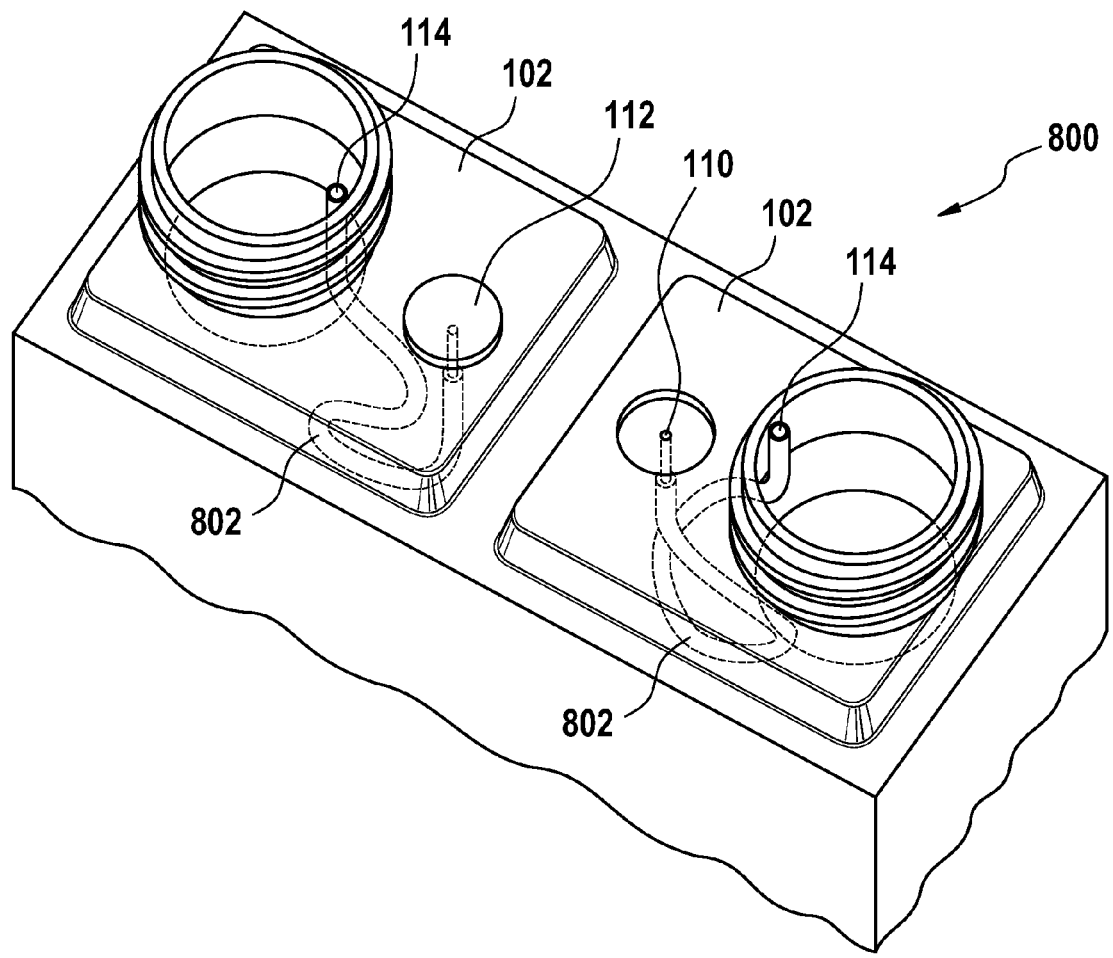
FIG. 9 illustrates the cartridge shown in FIG. 8 according to an embodiment of the present disclosure.

FIGS. 8 and 9 illustrate a cartridge 800 according to a further embodiment. In FIGS. 8 and 9, two cartridges can be integrated into a common housing. In this example, there can be a gas filter 112 mounted at the entrance to a tube 802. The tube can be located within the reservoir chamber 102. The tube can extend up to the top of threads upon which a cap 402 can be mounted. In this embodiment, the gas filter 112 can prevent fluid from leaving the cartridge 102 and also external particles or liquids, e.g., dust particles or droplets of condensed water, from entering and clogging the tube 802. FIG. 9 shows an example of the gas filter 112 removed on one of the cartridges 800. The caps 402 can also be removed in FIG. 9. It can be seen how the inlets 114 can be positioned in the reservoir chamber 102 at the highest point. The gas filters 112 can prevent fluid from exiting the reservoir chamber 102.

Figure 10:
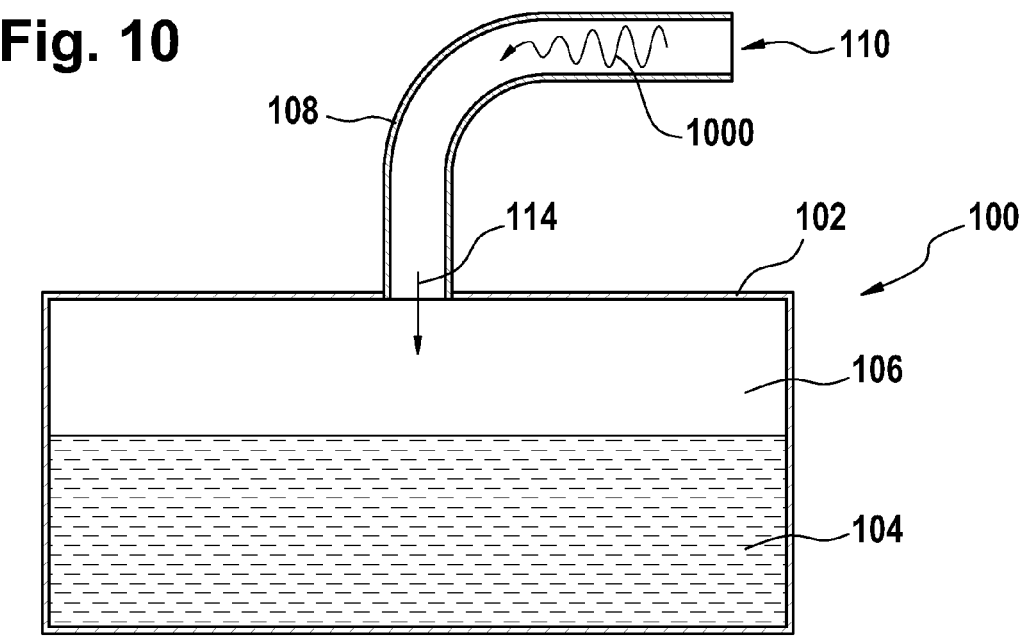
FIG. 10 illustrates a cartridge according to another embodiment of the present disclosure.

FIG. 10 shows another example of a cartridge 100. This example is used to discuss the diffusion of gas into the cartridge 100. The cartridge 100 can comprise a reservoir chamber 102 that can be partially filled with fluid 104 and gas 106. The baffle in this figure is represented by a tube 108. The baffle 108 can have a vent-to-atmosphere 110 and an inlet 114 which can enter the reservoir chamber 102 in the gas filled region 106. The line marked 1000 represents a gas molecule diffusing through the baffle means 108 to the inlet 114.

The cartridge shown in FIG. 10 can have both a gas and a liquid inside the reservoir chamber 102. Outside of the chamber can be atmospheric conditions. These two regions can be separated by a tube. The liquid in the cartridge can be progressively degraded by molecules in the atmospheric gases. These molecules can move from the surrounding environment to the inside of the cartridge by diffusion.

Calculations on how to define the tube diameter and length are detailed to demonstrate how to choose these parameters to prevent too fast destruction of the chemical properties of the liquid.

Basically the longer and the thinner the tube 108, the slower the diffusion of the molecule 1000 inside the cartridge can be. A general parameter, herein referred to as the impedance, can be defined and which can be used to perform calculations which assure than the cartridge can be usable during a certain time if it is kept open in the same environment. Z is defined as the ratio between the concentration difference of the molecule 1000 across the channel and the molecule flux multiplied by the diffusion constant D of molecule 1000 diffusing in the cartridge. This impedance can be easily calculated for long and round tube, and can be used as reference.

In order to make such calculations, it can be necessary to define or determine the conditions under which the liquid is no more usable due to the contamination or degradation by molecules from the environment. There is therefore a quantity, Ncrit, which can express the critical number of molecule 1000 which have diffused inside the reservoir. This quantity can depend highly on several parameters such as on solubility, and on different chemical reaction parameters, such as, temperature or pressure.

Important variables to define, concentrations are in molecule/$m^3$:

- t_life: wished duration time of the reservoir
- C_0: concentration of this molecule in surrounding environment
- N_crit: critical number of particles inside the cartridge which should never be attained during the time t_life.
- V_cart: Total volume of the cartridge
- V_gas: Volume of gas in the cartridge
- C_gas_0: initial concentration of the molecule in the gas part of the reservoir.
- D: is the diffusion constant of the molecule at the considered conditions
- Z: geometry inductance
- For round and long homogenous tube
  - L: length
  - S: cross-section surface (=$\pi R^Z$)

Z can be defined as the ratio between the concentration difference across the channel and the molecule flux multiplied by the diffusion constant D.

For a simple round and long geometry, the maximum molecule flow from the outside to the inside can be defined in the steady-state approximation:

$$\varphi_{max} = \frac{SD}{L}(C_0 - C_{gas\_0})(\text{molecule/s})$$

Therefore, by a simple integration, the maximum number of molecules in the cartridge at a time t, which have diffused inside:

$$Nmax(t) = \frac{SD}{L}(C_0 - C_{gas_0}) * t(\text{molecule})$$

Then we can deduce that we need this inequality:

$$N_{crit} \geq N_{max}(t_{life}) = \frac{SD}{L}(C_0 - C_{gas_0}) * t_{life}$$

In a more general way:

$$Ncrit \geq N_{max}(t_{life}) \geq \frac{D}{Z}(C_0 - C_{gas_0}) * t_{life}$$

To ensure with certitude a lifetime greater than t for the liquid inside the reservoir, the impedance Z has to respect this formula $$Z > D\frac{(C_0 - C_{gas\_0})t_{life}}{N_{crit}} = Zcrit$$

As written before, in the special case where the tubing is homogeneously round, Z can be defined by:

$$Z = \frac{L}{S}$$

Thus (for circular tubing):

$$\frac{L}{S} > D\frac{(C_0 - C_{gas\_0})t_{life}}{N_{crit}}$$

As long as the impedance Z of the tube is greater than Zcrit, the duration of the liquid and the cartridge can be preserved for a minimal time t.

Example: $CO_2$ in water

- D=0.16e-4 $m^2$/s
- V_cart=30 ml=30e-6 $m^3$
- T_life=1 year=365.25*24*3600 s
- $pCO_2$=4e-4*101325 (partial pressure of $CO_2$ in air)
- N_crit=N_crit_gas+N_crit_liq
  - N_crit_gas=Vgas*(Na*$pCO_2$)/(R*T)
    - With Na=Avogadro constant, R=perfect gas constant and T=temperature.
  - N_crit_liq=Vliq*MaxCon$CO_2$
    - This value is taken to be around 120 mg/l, which is a lot more than for the N_crit_gas The critical number of $CO_2$ molecules in gas can be attained when the partial pressure in the gas volume is attained and $CO_2$ molecules are saturated in water (approx. double the number needed to saturate gas).

For one year stability:

- Vliq=29 ml
  - L=100 cm and D=3.2 mm
  - L=10 cm and D=1 mm
- Vliq=15 ml
  - L=100 cm and D=2.3 mm
  - L=10 cm and D=726 μm
- Vliq=1 ml
  - L=100 cm and D=650 μm
  - L=10 cm and D=205 μm Vliq can be the volume of the liquid or fluid in the reservoir chamber. If length and diameter values of the tube are chosen so that the impedance is above these values then the cartridge can have the desired life time of one year. For instance, in one embodiment, the baffle comprises a tube with a length greater than or equal to 10 cm with a diameter equal to or less than 1 mm. For a tube of 10 cm in length with a diameter of 1 mm, Z=1.24e5 $m^{-1}$. In one embodiment, the impedance, as defined above, of the baffle can be less than or equal to 1.24e5 $m^{-1}$. In this embodiment, the fluid may be a creatinine test reagent.

Similarly, for 15 ml of liquid in the reservoir chamber, with 1 ml of gas in the cartridge, and considering CO2 diffusion, the length of the tube can be at least 10 cm with a diameter of less than or equal to 726 μm. In one embodiment, the impedance, as defined above, of the baffle can be less than or equal to $Z=12.42e5$ m$^{-1}$. In this embodiment, the fluid may be a creatinine test reagent.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A cartridge for dispensing a fluid, the cartridge comprising:
    a reservoir chamber for receiving the fluid and for receiving a ventilation gas, wherein the reservoir chamber comprises an inlet for receiving the ventilation gas and an outlet for dispensing the fluid, wherein at least a portion of the reservoir chamber is filled with the ventilation gas when in an operating position, wherein the inlet is located in the portion filled with the ventilation gas, and wherein the fluid comprises a reagent; and
    a baffle for restricting gas diffusion through the inlet, wherein the reservoir chamber receives the ventilation gas via the baffle, wherein the inlet is attached to the baffle and maintains a constant gas pressure within the portion of the reservoir chamber that is filled with the ventilation gas, and wherein the baffle is adjacent to and at least partially formed on an exterior surface of the cartridge.

2. The cartridge of claim 1, wherein the inlet maintains a constant gas pressure within the portion of the reservoir chamber that is filled with the ventilation gas when the reservoir chamber is between 10 percent and 90 percent full with the fluid.

3. The cartridge of claim 1, wherein the inlet maintains a constant gas pressure within the portion of the reservoir chamber that is filled with the ventilation gas when the reservoir chamber is between 20 percent and 80 percent full with the fluid.

4. The cartridge of claim 1, wherein the dispenser dispenses fluid at a rate independent of the baffle.

5. The cartridge of claim 1, further comprises, a cap for sealing the inlet.

6. The cartridge of claim 5, wherein the cap moves to an open position to open the inlet.

7. The cartridge of claim 6, wherein the cap re-seals the inlet.

8. The cartridge of claim 5, wherein the cartridge forms at least a portion of the baffle when the cap is opened.

9. The cartridge of claim 5, wherein the cartridge comprises threads for attaching the cap.

10. The cartridge of claim 9, wherein the baffle comprises a diffusion path formed in the threads.

11. The cartridge of claim 10, wherein the diffusion path comprises a channel in the threads, and wherein the cartridge further comprises a cap restraint for limiting the opening of the cap a predetermined amount.

12. The cartridge of claim 5, wherein the baffle comprises a tube located at least partially within the reservoir chamber, wherein the tube comprises an opening and the inlet, and wherein the cap seals the inlet within the reservoir chamber.

13. The cartridge of claim 5, wherein the cap is attached to cartridge.

14. The cartridge of claim 5, wherein the cap is removable from the cartridge.

15. The cartridge of claim 5, wherein the cap is movable between an open position and a closed position, and wherein when in the open position, the cap opens the baffle.

16. The cartridge of claim 1, wherein the baffle comprises a tube located at least partially within the reservoir chamber.

17. The cartridge of claim 1, wherein the baffle comprises a tube mounted on the exterior surface.

18. The cartridge of claim 1, wherein the baffle is at least partially formed within the reservoir chamber.

19. The cartridge of claim 1, wherein at least a part of the cartridge is injection molded, and wherein the baffle is formed at least partially by the part.

20. The cartridge of claim 1, wherein the baffle comprises a gas filter.

21. The cartridge of claim 1, further comprises, the fluid.

22. The cartridge of claim 1, wherein the fluid comprises any one of the following: a blood grouping reagent, a solvent, a diluent, a catalyst, an antibody, an enzyme, a recombinant protein, a virus isolate, a virus, a biological reagent, a protein, a salt, a detergent, a nucleic acid, an acid, a base, a dispersion, latex particles, nano particles, magnetic particles, and combinations thereof.

23. The cartridge of claim 1, further comprises,
    a dispenser for dispensing the fluid, and wherein the dispenser receives the fluid from the outlet.

24. The cartridge of claim 23, wherein the dispenser is a micro-fluidic dispensing assembly.

25. The cartridge of claim 23, wherein the dispenser dispenses any one of the following: volumes less than 10 µL, less than 500 nL, less than 200 nL, less than 100 nL, and less than 20 nL.

* * * * *